United States Patent [19]
Gilmore et al.

[11] Patent Number: 5,563,147
[45] Date of Patent: Oct. 8, 1996

[54] SEROTONERBIC TETRAHYDROPYRIDOINDOLES

[75] Inventors: Jeremy Gilmore, Frimley; Peter T. Gallagher, Camberley; Martin V. Miles, Twickenham; William M. Owton, Lightwater; Colin W. Smith, Bracknell, all of United Kingdom

[73] Assignee: Eli Lilly and Company, Indianapolis, Ind.

[21] Appl. No.: 462,237

[22] Filed: Jun. 5, 1995

[30] Foreign Application Priority Data

Sep. 12, 1994 [GB] United Kingdom ............ 9418326

[51] Int. Cl.$^6$ .................. A61K 31/44; C07D 471/04
[52] U.S. Cl. ................ 514/292; 546/85; 546/86; 546/87
[58] Field of Search ................ 546/85, 86; 514/292

[56] References Cited

U.S. PATENT DOCUMENTS

| | | | |
|---|---|---|---|
| 4,035,369 | 7/1977 | Vandenberk et al. | 260/293.6 |
| 4,254,127 | 3/1981 | Vandenberk et al. | 424/263 |
| 4,432,978 | 2/1984 | Welch et al. | 546/85 |
| 4,547,507 | 10/1985 | Rowlands et al. | 514/291 |
| 4,680,296 | 7/1987 | Manoury et al. | 514/259 |
| 4,789,676 | 12/1988 | Hilbert et al. | 546/85 |
| 5,434,148 | 7/1995 | Yamada et al. | 514/213 |

FOREIGN PATENT DOCUMENTS

| | | | |
|---|---|---|---|
| 0099303 | 1/1984 | European Pat. Off. | 495/4 |
| 0144729A1 | 6/1985 | European Pat. Off. | 498/4 |
| 0445862A2 | 9/1991 | European Pat. Off. | 405/12 |
| 0454330A1 | 10/1991 | European Pat. Off. | 235/26 |
| WO91/16323 | 10/1991 | WIPO | 471/4 |

OTHER PUBLICATIONS

Gueremy, et al., *Naphthosultam derivatives as serotonin antagonists*, Derwent WPI abstract (91–339733/46) 1991.

*Primary Examiner*—Johann Richter
*Assistant Examiner*—Laura L. Stockton
*Attorney, Agent, or Firm*—Robert D. Titus; Joseph J. Jones; David E. Boone

[57] ABSTRACT

This invention provides novel, optionally substituted tetrahydropyridoindoles which are useful serotonergic agents for the treatment of central nervous system disorders.

8 Claims, No Drawings

SEROTONERBIC TETRAHYDROPYRIDOINDOLES

This invention relates to pharmaceutical compounds, their preparation and use.

The compounds of the invention are of the formula:

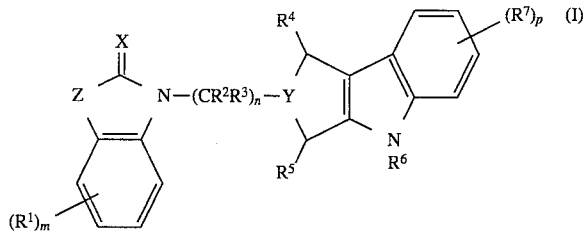

in which $R^1$ and $R^7$ are each halo, trifluoromethyl, $C_{1-6}$ alkyl, $C_{1-6}$ alkoxy, optionally substituted phenyl, optionally substituted naphthyl or optionally substituted heteroaryl, $R^2$ and $R^3$ are each hydrogen or $C_{1-6}$ alkyl, $R^4$ and $R^5$ are each hydrogen, halo, trifluoromethyl, $C_{1-6}$ alkyl, $C_{1-6}$ alkoxy, optionally substituted phenyl, optionally substituted naphthyl or optionally substituted heteroaryl, $R^6$ is hydrogen, $C_{1-6}$ alkyl, optionally substituted phenyl, optionally substituted naphthyl, optionally substituted heteroaryl, optionally substituted phenyl-$C_{1-6}$ alkyl or —$CO_2R^8$ where $R^8$ is an ester group, m and p are each 0, 1, 2, 3 or 4, n is 1, 2, 3 or 4, Z is

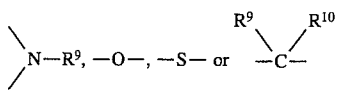

where $R^9$ and $R^{10}$ are each hydrogen, $C_{1-6}$ alkyl or optionally substituted phenyl-$C_{1-6}$ alkyl, X is oxygen or sulphur, and Y is

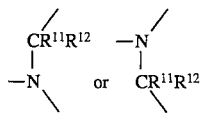

where $R^{11}$ and $R^{12}$ are each hydrogen, $C_{1-6}$ alkyl, trifluoromethyl, optionally substituted phenyl, optionally substituted naphthyl or optionally substituted heteroaryl;
and salts and solvates thereof.

The compounds of the invention are indicated for use in the treatment of diseases of the central nervous system. They are active in tests that indicate serotonergic modulation.

Formula (I) above comprises two groups of compounds:

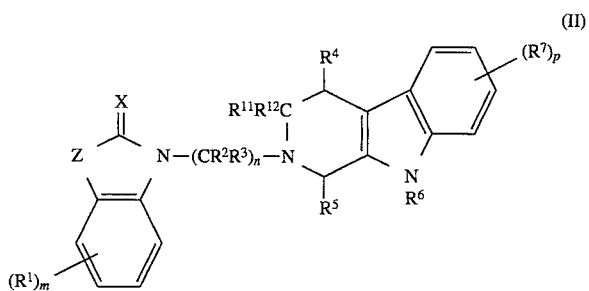

and

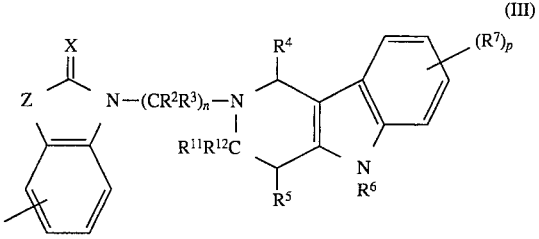

of which (II) is preferred.

A preferred group of compounds is of the formula

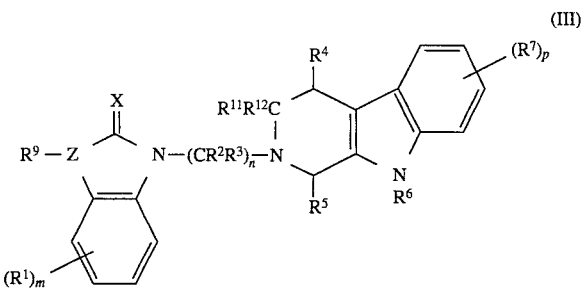

In the above formula (I), a $C_{1-6}$ alkyl group includes methyl, ethyl, propyl, isopropyl, butyl, tert. butyl, pentyl and hexyl, and is preferably methyl or ethyl. A $C_{1-6}$ alkoxy group is one such alkyl group linked to a ring via an oxygen atom, and a halo atom is preferably chlorine, bromine or fluorine, and especially chlorine or fluorine.

A substituted phenyl group is phenyl substituted with one or more, for example one to three, substituents selected from, for example, $C_{1-4}$ alkyl, especially methyl, $C_{1-4}$ alkoxy, especially methoxy and ethoxy, hydroxy, nitro, cyano, halo, especially chloro or fluoro, trihalomethyl, especially trifluoromethyl, carboxy and $C_{1-4}$ alkoxy-carbonyl. A substituted phenyl-$C_{1-6}$ alkyl group has one or more of these substituents on the phenyl ring, and is preferably substituted benzyl. A substituted naphthyl or heteroaryl may also be substituted with one or more of the above substituents. An optionally substituted phenyl-$C_{1-6}$ alkyl group is preferably benzyl.

An ester group can be aliphatic or aromatic and the most preferred esters are alkyl esters derived from $C_{1-4}$ alkanols, especially methyl and ethyl esters.

A heteroaryl group can have one or more hetero atoms selected from, for example, oxygen, nitrogen and sulphur and preferably contains from 5 to 10 carbon atoms. Preferably a heteroaryl group is of the formula:

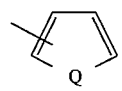

where Q is —O—, —S— or —NR—, and R is hydrogen or $C_{1-6}$ alkyl. Alternatively, a heteroaryl group can comprise a benzene fused ring as, for example:

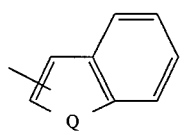

Further heteroaryl groups include those of the formula:

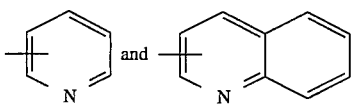

Preferred compounds are those having one or more of the following features:
(i) X is oxygen.
(ii) Z is

and
$R^9$ is hydrogen or $C_{1-6}$ alkyl.
(iii) $R^9$ is hydrogen.
(iv) $R^1$ is halo, $C_{1-6}$ alkyl or $C_{1-6}$ alkoxy.
(v) m is 0, 1 or 2.
(vi) p is 0, 1 or 2.
(vii) $R^2$ and $R^3$ are hydrogen.
(viii) $R^4$ is hydrogen.
(ix) $R^5$ is hydrogen, trifluoromethyl or $C_{1-6}$ alkyl.
(x) $R^5$ is hydrogen.
(xi) $R^6$ is hydrogen.
(xii) $R^7$ is halo, trifluoromethyl, $C_{1-6}$ alkyl or $C_{1-6}$ alkoxy.
(xiii) $R^{11}$ and $R^{12}$ are hydrogen.

When there is more than one $R^1$ or more than one $R^7$ substituent, it is to be understood that they can be the same or different. Also, when n is 2, 3 or 4, the values of $R^2$ and $R^3$ attached to each carbon atom need not be identical.

A preferred group of compounds is of the formula:

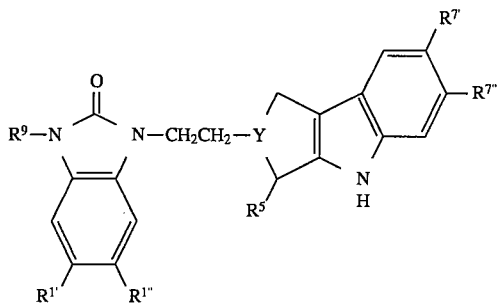

in which $R^9$ is hydrogen or $C_{1-6}$ alkyl, $R^{1'}$, $R^{1''}$, $R^{7'}$ and $R^{7''}$ are each hydrogen, halo, $C_{1-6}$ alkyl or $C_{1-6}$ alkoxy, $R^5$ is hydrogen or trifluoromethyl, and Y is:

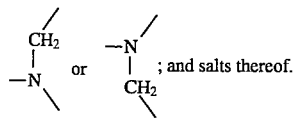 ; and salts thereof.

It will be appreciated that the compounds of the invention can contain one or more asymmetric carbon atoms which gives rise to isomers. The compounds are normally prepared as racemic mixtures and can conveniently be used as such, but individual isomers can be isolated by conventional techniques if so desired. Such racemic mixtures and individual optical isomers form part of the present invention. It is preferred to use an enantiomerically pure form.

It is, of course, possible to prepare salts of the compounds of the invention and such salts are included in the invention. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

In addition to pharmaceutically-acceptable salts, other salts are included in the invention. They may serve as intermediates in the purification of compounds or in the preparation of other, for example pharmaceutically-acceptable, acid addition salts, or are useful for identification, characterisation or purification.

The invention also includes solvates, for example, ether solvates such as, for instance, solvates formed with dioxan and tetrahydrofuran, or alcohol solvates such as, for instance, solvates from methanol and ethanol.

The invention also includes a process for producing a compound of formula (I) above, which comprises reacting a compound of the formula:

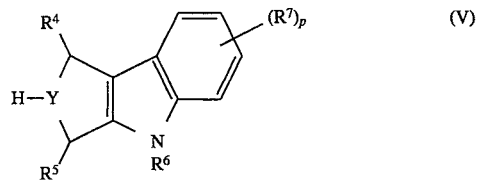 (V)

where H—Y is:

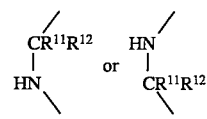

and $R^5$, $R^6$, $R^7$, $R^8$, $R^{10}$, $R^{11}$ and p have the values given above, with a compound of the formula:

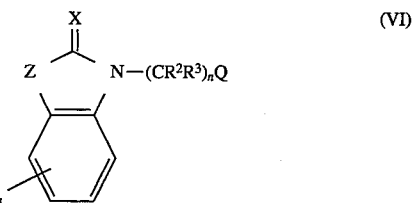 (VI)

where Q is a leaving group, for example halo, or a mesylate or tosylate, and Z, X, $R^1$, $R^2$, $R^3$ and n and m have the values given above.

The reaction is preferably carried out in an inert organic solvent such as, for example, methyl isobutyl ketone or acetonitrile, and at a temperature of from 80° C. to 110° C. The reaction takes place in alkaline conditions by the use of, for example, sodium carbonate or potassium carbonate.

Compounds of formula (V) are either known or can be prepared by methods well known in the art. For example, compounds of formula (V) which are tetrahydro-pyridoindoles in which H—Y is

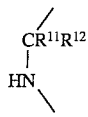

can be prepared by reacting the appropriate hydrazine with N-protected piperidin-3-one as for instance:

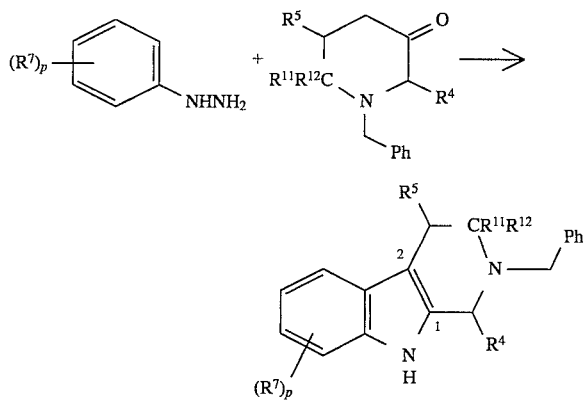

with potassium carbonate, followed by acetic and hydrochloric acids, and then alkali. Removal of the protecting group is carried out by hydrogenation with palladium and charcoal.

Tetrahydro-pyrido-indole intermediates in which

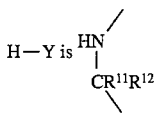

can be prepared in a similar manner employing an appropriate N-protected piperidin-4-one, for example, of formula:

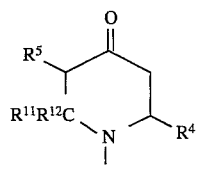

The haloethyl benzimidazolone and thione compounds of formula (VI) are either known compounds or can be made by standard procedures, as for example reacting a compound of the formula:

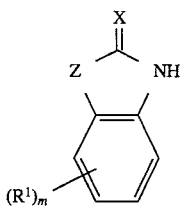

with a compound of formula Q' $(CR^2R^3)_n$Q where Q' is a leaving group.

An alternative route to the compounds of the invention consists of an analogous, reverse, condensation of the two principal components of the molecule, as for example by reacting a compound of the formula:

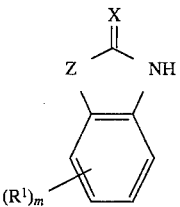

with a compound of the formula:

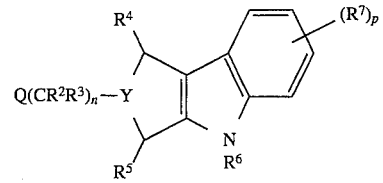

Such reagents can be made as described above or by analogous methods.

It will be appreciated that when one or more of $R^9$, $R^{10}$ and $R^6$ is other than hydrogen, groups can be attached at these positions by alkylation.

As mentioned above, the compounds of the invention have useful central nervous system activity. The compounds are active at the serotonin, 5-$HT_{1D\alpha}$, receptor. Their binding activity has been demonstrated in a test described by Zgombick, J. M. et al., Molecular Pharmacology Vol. 40 1992, pages 1036–1042, and compounds of the invention as described in the following Examples have a Ki of from 20 nM to 5,000 nM. Some of the compounds, for example those of formula III, also possess binding activity at the 5-$HT_{1D\beta}$ receptor. Furthermore, compounds have activity at the 5-HT2A receptors as shown in the test described by Leysen, J. E. et al., Molecular Pharmacology Vol. 21 1981, pages 301–314.

Because of their selective affinity for the 5-HT receptors, the compounds of the present invention are indicated for use in treating a variety of conditions such as obesity, bulimia, alcoholism, pain, depression, hypertension, ageing, memory loss, sexual dysfunction, anxiety, schizophrenia, gastrointestinal disorders, headache, cardiovascular disorders, smoking cessation, drug addiction and emesis.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mg/kg per day, for example in the treatment of adult humans, dosages of from 0.5 to 100 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt or solvate thereof, associated with a pharmaceutically acceptable excipient. In making the compositions of the invention, the active ingredient will usually be mixed with a carrier, or diluted by a carrier, or enclosed within a carrier which may be in the form of a capsule, sachet, paper or other container. The excipient may be a solid, semi-solid or liquid material which acts as a vehicle, excipient or medium for the active ingredient. Some examples of suitable excipients are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions or suspensions for parenteral use or as suppositories. Preferably the compositions are formulated in a dosage unit form, each dosage containing from 0.5 to 100 mg, more usually 1 to 100 mg, of the active ingredient.

The following Examples illustrate the invention:

EXAMPLE 1

1-[2-(1,2,3,4-Tetrahydro-9H-pyrido[3,4-b]indol-2-yl)-1-ethyl]-1,3-dihydro-benzimidazol-2-one 1,2,3,4-Tetrahydro-9H-pyrido[3,4-b]indole (1.50 g, 8.7 mmol) was suspended in methyl isobutyl ketone (50 ml). 1-(2-Chloroethyl)-1,3-dihydro-2H-benzimidazol-2-one (1.958 g, 9.58 mmol) was added to the mixture along with sodium carbonate (1.110 g, 10.45 mmol) and tetrabutyl ammonium iodide (10 mg). The suspension was heated to 90° C. for 2 days, under an inert ($N_2$) atmosphere. The mixture was concentrated in vacuo to dryness. Water (70 ml) was added, followed by addition of 2N HCl to pH1. The mixture was extracted with $CHCl_3$ (2×70 ml), basified to pH10 using 5N NaOH, and again extracted with $CHCl_3$ (3×70 ml). The organics were combined and washed with brine, separated and dried over $MgSO_4$. The resulting solid was purified by chromatography ($CHCl_3$, MeOH (2%)) to yield a yellow solid, m.p. 214°–216° C.

EXAMPLE 2

2((3,3-Dimethyl)oxindolyl) ethanol 3,3-Dimethyl oxindole (1.1 equivalent) was dissolved in dry dimethyl formamide. Sodium hydride (60% dispersion in mineral oil) (1.1 equivalent) was added portionwise and the mixture was stirred under nitrogen for one hour at 25° C. 2-(2-Chloroethoxy)tetrahydro-2H-pyran (1 equivalent) was added with a catalytic amount of sodium iodide. The reaction mixture was stirred under nitrogen at 70° C. for 12 hours, then the solvent was removed under reduced pressure. The resulting oil was partitioned between ethyl acetate and water. The organic phase was dried ($MgSO_4$), filtered and evaporated to dry under reduced pressure. The resulting oil was taken up in methanol and stirred at room temperature with paratoluenesulfonic acid. After eight hours the solvent was removed and replaced with ethyl acetate. The solution was washed (×2) with saturated sodium hydrogen carbonate solution, dried ($MgSO_4$), filtered and evaporated to dryness. Column chromatography of the resulting oil on silica gel (eluent ethyl acetate/hexane 1:1) gave 2((3,3-dimethyl)oxindolyl)ethanol.

1-(2-(1,2,3,4-Tetrahydro-9H-pyrido[3,4-b]indol-2-yl)-1-ethyl)-1,3-dihydro-3,3-dimethyl-2H-indol-2-one 2-((3,3-Dimethyl)oxindolyl)ethanol and triethylamine (1.1 equivalent) were dissolved in dichloromethane, cooled to 0° C. under nitrogen with stirring and methanesulfonyl chloride (1 equivalent) was added. The mixture was stirred for 30 minutes, washed with cold dilute hydrochloric acid, dried ($MgSO_4$), filtered and concentrated to dryness. The resulting oil was dissolved in acetonitrile and added to a solution of tetrahydro-β-carboline (1 equivalent) containing potassium carbonate (2.5 equivalent) and potassium iodide (0.1 equivalent). The reaction mixture was heated under reflux for three days under nitrogen. The solvent was removed under reduced pressure and the residue taken up in ethyl acetate. This solution was washed (×2) with water, dried ($MgSO_4$), filtered and concentrated to dry under reduced pressure. Chromatography on silica gel (eluent ethyl acetate/methanol) gave an oil which was taken up in ethyl acetate. Maleic acid (1 equivalent) was added. The suspension was refrigerated for 12 hours and the white crystals collected to given 1-(2-(1,2,3,4-tetrahydro-9H-pyrido[3,4-b] indol-2-yl)-1-ethyl)-1,3-dihydro-3,3-dimethyl-2H-indol-2-one as its monomaleate salt, melting point 156°–158° C.

1-(2-(2,3,4,5-Tetrahydro-1H-pyrido[4,3-b]indol-2-yl)-1-ethyl)-1,3-dihydro-3,3-dimethyl-2H-indol-2-one This compound was prepared from tetrahydro-γ-carboline and 2((3,3-dimethyl)oxindolyl)ethanol by the above method and was isolated as its monomaleate salt, melting point 111°–114° C.

1-(2-Methyl)-1,2,3,4-tetrahydro-9H-pyrido[3,4-b]indol-2-yl]-1-ethyl)-1,3-dihydro- 2H-benzimidazol-2-one This compound was prepared from-1-chloroethylbenzimidazolone and racemic tetrahydroharman (JCS Perk I (1983) 265) by the standard method and isolated as its monomaleate salt, melting point 174°–176° C.

1-(2-(3-Methyl)-1,2,3,4-tetrahydro-9H-pyrido[3,4-b]indol-2-yl)-1-ethyl)- 1,3-dihydro-2H-benzimidazol-2-one This compound was prepared from 1-chloroethylbenzimidazolone and 3-methyl-1,2,3,4-β-carboline (Chem. Abs. 59 7501 g) by the standard method and isolated as its hydrochloride salt, melting point 183°–186° C.

EXAMPLE 3

6-Chloro-1-(2-(1,2,3,4-tetrahydro-9H-pyrido[3,4-b]indol-2-yl)-ethyl)- 1,3-dihydro-2H-benzimidazol-2-one Sodium carbonate (0.403 g, 3.8 mmol) was added to a mechanically stirred suspension of 6-chloro-1-(2-mesyloxyethyl)- 1,3-dihydro-2H -benzimidazol-2-one (1 g, 3.443 mmol) (U.S. Pat. No. 4,035,369) in isobutylmethylketone (30 ml) and heated and mechanically stirred for 24 hours under reflux under nitrogen, cooled, the solvent evaporated in vacuo and the residue partitioned between water (100 ml) and ethyl acetate (100 ml), the aqueous re-extracted with ethyl acetate (2×100 ml), combined, washed with water and dried ($MgSO_4$). The magnesium sulfate was removed by filtration and the filtrate evaporated in vacuo to give an orange-yellow residue which was triturated with diethyl ether to give a yellow solid. This solid was chromatographed on flash silica (MeOH/$CHCl_3$ 5:95) to give the benzimidazolone, melting point 138°–140° C.

EXAMPLE 4

3-(Mesyloxyethyl)benzothiazolin-2-one

Methanesulfonyl chloride (1.625 ml, 2.4 g, 21 mmol) in dichloromethane (10 ml) was added dropwise with stirring to 3-(2-hydroxyethyl)benzothiazolin-2-one (3.9 g, 20 mmol) (J. J. D'Amico and F. G. Bollinger; J. Heterocyclic Chemistry 1988, 25, 1601).and triethylamine (3.478 ml, 2.525 g, 25 mmol) in dichloromethane (80 ml) and stirred for one hour at room temperature. The reaction mixture was then washed with water and dried ($MgSO_4$), filtered and the solvent evaporated in-vacuo to give the title product.

3-(2, (1,2,3,4-Tetrahydro-9H-pyrido[3,4-b]indol-2-yl)-ethyl)-1,3-dihydrobenzothiazolin-2-one Potassium carbonate (1.105 g, 8.00 mmol) was added to 1,2,3,4-tetrahydro-9H-pyrido[3,4-b]indole (1.144 g, 6.65 mmol) and 3-(2-mesyloxyethyl)benzothiazolin-2-one (1.815 g, 6.648 mmol) in acetonitrile (50 ml) and heated and mechanically stirred under nitrogen under reflux for 24 hours. The excess acetonitrile was evaporated in vacuo to give a white solid which was partitioned between ethyl acetate and water (150 ml 1:1) and then separated. The aqueous layer was extracted with more ethyl acetate (75 ml) and the ethyl acetate fractrons combined, washed with water and dried (MgSO$_4$). The solvent (ethyl acetate) was evaporated in vacuo to give a yellow solid, which was chromatographed on flash silica, eluting with ethyl acetate, to give the title product, melting point 109°–111° C.

EXAMPLE 5

3-(2-Mesyloxyethyl)benzoxazolin-2-one

Methanesulfonyl chloride (2.21 ml, 3.265 g, 28.5 mmol) was added to a stirred solution of 3-(2-hydroxyethyl)benzoxazolin-2-one (5 g, 27.933 mmol) (J. Heterocyclic Chemistry 1988, 25, 1601) and triethylamine (5.947 ml, 4.318 g, 42.75 mmol) in dichloromethane (60 ml) and stirred for three days at room temperature. The solvent was evaporated in vacuo and the residue partitioned between water and ethyl acetate, washed with hydrochloric acid (2M, 5×50 ml), sodium hydrogen carbonate (2×20 ml), dried (MgSO$_4$), filtered and the solvent removed in vacuo to give the title product.

3-(2-(1,2,3,4-Tetrahydropyrido[3,4-b]indol-2-yl)ethyl)benzoxazolin-2-one

Potassium carbonate (0.828 g, 6 mmol), 3-(2-mesyloxyethyl)benzoxazolin-2-one (1.494 g, 5.814 mmol) and 1,2,3,4-tetrahydropyrido[3,4-b]indole (1 g, 5.814 mmol) in acetonitrile (30 ml) were heated under reflux under nitrogen for 16 hours. The solvent was evaporated in vacuo and the residue partitioned between ethyl acetate (80 ml) and water (30 ml). The water was separated and hydrochloric acid (0.5M, 40 ml) was added. The resultant white precipitate was collected by filtration and suspended in sodium hyroxide (2M, 60 ml) and washed with chloroform (3×50 ml). The combined chloroform extracts were washed with water (30 ml), dried (MgSO$_4$), and the solvent filtered and evaporated in vacuo. The residue was treated with diethyl ether/ethyl acetate (3:1, 40 ml) and a fine flocculent precipitate resulted. The resultant filtrate was evaporated in vacuo and the residue chromatographed on silica (ethyl acetate 40–60 petrol 3:2) to give the title product, melting point 135°–137° C.

EXAMPLE 6

2-t-Butoxycarbonyl-1,2,3,4-tetrahydropyrido[3,4-b]indole

Di-t-butyldicarbonate (6.35 g, 29.09 mmol) was added to a 2-phase mixture of 1,2,3,4-tetrahydropyrido[3,4-b]indole (5 g, 29.07 mmol) in 2M sodium hydroxide (100 ml) and dichloromethane (80 ml) and stirred at room temperature for 20 hours. The dichloromethane layer was separated and the aqueous extracted with dichloromethane (120 ml). The aqueous was separated and the dichloromethane layers combined, washed with 1M hydrochloric acid (100 ml), sodium hydrogen carbonate solution and dried (MgSO$_4$). The magnesium sulfate was collected by filtration and the filtrate evaporated in vacuo to give the protected beta carboline.

2-t-Butoxycarbonyl-9-methyl-1,2,3,4-tetrahydropyrido[3,4-b]indole 2-t-Butoxy carbonyl-1,2,3,4-tetrahydropyrido[3,4-b]indole (2 g, 7.353 mmol) in THF (25 ml) was added dropwise with stirring under nitrogen to a suspension of sodium hydride in oil dispersion (50% 0.388 g; 0.194 g 8.088 mmol). After one hour, DMF (5 ml) was added and the mixture stirred for 30 minutes when iodomethane (0.546 ml, 1,245 g, 8.088 mmol) was added. After two hours more iodomethane (2 ml, 4.56 g, 29.626 mmol) was added and the mixture stirred at room temperature for 16 hours. The mixture was then partitioned between water (150 ml) and ethyl acetate (150 ml), and the aqueous layer re-extracted with ethyl acetate (2×50 ml). The ethyl acetate extracts were combined, washed with dilute hydrochloric acid (1M, 2×50 ml), water, and dried (MgSO$_4$). The magnesium sulfate was collected by filtration and the filtrate evaporated in vacuo to give the methylated beta carboline.

9-Methyl-1,2,3,4-tetrahydropyrido[3,4-b]indole

Trifluoroacetic acid (3.5 ml, 45.23 mmol) was added to a solution of 2-t-butoxycarbonyl-9-methyl-1,2,3,4-tetrahydropyrido[3,4-b]indole (1.848 g, 6.461 mmol) in dichloromethane (25 ml) and stirred at room temperature for 3 hours, diluted with dichloromethane (125 ml), washed with 2M sodium hydroxide (2×50 ml), water and dried (MgSO$_4$). The magnesium sulfate was collected by filtration and the filtrate evaporated in vacuo to give the title product.

9-Methyl-1-(2-(1,2,3,4-tetrahydro-9H-pyrido[3,4-b]indol-2-yl)ethyl-1,3-dihydro-2H-benzimidazol-2-one Tetra-n-butylammonium iodide (100 mg) was added to a mechanically stirred mixture of 9-methyl-1,2,3,4-tetrahydro-9H-pyrido[3,4-b]indole (1.08 g, 5.81 mmol), 1-(2-chloroethyl)- 1,3-dihydro-2H-benzimidazol-2-one (1.14 g 5.81 mmol), sodium carbonate (0.6625 g, 6.25 mmol) and isobutylmethylketone (30 ml) and heated at 90° C. for 24 hours, cooled, and allowed to stand for 48 hours. The solvent was evaporated in vacuo, and the residue partitioned between water and ethyl acetate, the ethyl acetate dried (MgSO$_4$), filtered and the solvent evaporated in vacuo. The resultant residue was impure and was purified by prep hplc (60% acetonitrile 40% water 0.1% NH$_3$) to give the product, melting point 166°–167° C. (toluene).

EXAMPLE 7

1-Phenylmethyl-3-[2-(1,2,3,4-tetrahydro-9H-pyrido[3,4-b] indol-2-yl)-1-ethyl]-1,3-dihydro-2H-benzimidazol-2-one monohydrochloride 1-[2-(1,2,3,4-Tetrahydro-9H-pyrido[3,4-b]indol-2-yl)-1-ethyl]-1,3-dihydro-2H-benzimidazol-2-one (1.0 g, 3.0 mmol) was dissolved in DMF (10 ml). 60% Sodium hydride (0.132 g, 3.3 mmol) was added and the mixture was stirred at ambient temperature under nitrogen for 10 minutes. Benzyl bromide (0.39 ml, 3.31 mmol) was added and the solution was stirred at ambient temperature for 24 hours.

The mixture was concentrated in vacuo and water (50 ml) was added. The precipitate was extracted into chloroform (3×50 ml), dried over magnesium sulphate, filtered and concentrated in vacuo. The resulting solid was taken up in ethyl acetate (20 ml) and hydrogen chloride gas was bubbled through. The resultant precipitate was recrystallised from methanol/diethyl ether to yield a cream-coloured precipitate, melting point 215°–217° C.

The following compound was prepared in a similar way:

1-Methyl-3-[2-(1,2,3,4-tetrahydro-9H-pyrido[3,4-b]indol-2-yl)-1-ethyl]-1,3-dihydro-2H-benzimidazol-2-one, melting point 182°–184° C. (isolated as the hydrochloride).

EXAMPLE 8

7-Fluoro-1,2,3,4-tetrahydro-9H-pyrido[3,4-b]indole

6-Fluorotryptamine hydrochloride (0.511 g, 2.38 mmol) was dissolved in water (9 ml). Glyoxylic acid monohydrate (0.241 g, 2.618 mmol) was added, followed by KOH (0.129 g, 2.31 mmol). The resultant solid was stirred at ambient temperature for one hour before concentrated HCl (0.6 ml) was added in one portion. The mixture was refluxed for 30 minutes, more concentrated hydrogen chloride (0.6 ml) was added and the mixture was again refluxed for 15 minutes. The mixture was cooled to room temperature and basified to pH12 using 5N sodium hydroxide. It was extracted with chloroform (4×75 ml), separated, dried over magnesium sulphate, filtered and concentrated in vacuo to yield an off-white solid.

The following compounds were prepared in a similar way (see also European Patent Application No. 94302608.8, Publication 0 620 222):

7-Methyl-1,2,3,4-tetrahydro-9H-pyrido[3,4-b]indole

7-Methyl-8-bromo-1,2,3,4-tetrahydro-9H-pyrido[3,4-b]indole

6-Methyl-8-chloro-1,2,3,4-tetrahydro-9H-pyrido[3,4-b]indole

6-Fluoro-1,2,3,4-tetrahydro-9H-pyrido[3,4-b]indole

1-[2-(6-Methoxy-1,2,3,4-tetrahydro-9H-pyrido-[3,4-b]-indol-2-yl)ethyl]-1,3-dihydro-2H-benzimidazol-2-one 6-Methoxy-1,2,3,4-tetrahydro-9H-pyrido-[3,4-b]indole (1.5 g, 7.42 mmol) was suspended in methyl isobutyl ketone (35 ml), To this was added 1-chloroethyl-1,3-dihydro-2H-benzimidazol-2-one (1.605 g, 8.16 mmol), sodium carbonate (0.944 g, 8.904 mmol), and tetrabutyl ammonium iodide (0.030 g). The mixture was warmed to 90° C. under nitrogen for two days. The mixture was concentrated in vacuo, taken up in water (75 ml) and extracted with chloroform (3×50 ml). It was dried over $MgSO_4$, filtered and concentrated in vacuo. The resulting oil was purified by chromatography using flash silica, chloroform and methanol to yield a yellow solid, melting point 116°–117° C.

The following compounds were prepared in a similar way:

1-[2-(6-Fluoro-1,2,3,4-tetrahydro-9H-pyrido(3,4-b)indol-2-yl)-1-ethyl]-1,3-dihydro-2H-benzimidazol-2-one, melting point 115°–117° C.

1-[2-(8-Chloro-6-methyl-1,2,3,4-tetrahydro-9H-pyrido(3,4-b)-indol-2-yl)-1-ethyl]-1,3-dihydro-2H-benzimidazol-2-one, melting point 188°–189° C.

1-[2-(8-Bromo-7-methyl-1,2,3,4-tetrahydro-9H-pyrido(3,4-b)-indol-2-yl)-1-ethyl]-1,3-dihydro-2H-benzimidazol-2-one, melting point 141°–143° C.

1-[2-(7-Fluoro-1,2,3,4-tetrahydro-9H-pyrido(3,4-b)indol-2-yl)-1-ethyl]-1,3-dihydro-2H-benzimidazol-2-one, melting point 104°–106° C.

EXAMPLE 9

6-Hydroxymethyl indole

Lithium aluminium hydride (3.48 g, 91.70 mmol) was suspended in sodium-dried tetrahydrofuran (150 ml). The suspension was stirred under a nitrogen atmosphere. Methyl-(indol-6-yl)methanoate (8.0 g, 45.7 mmol) was dissolved in dry tetrahydrofuran (50 ml) and added dropwise to the lithium aluminium hydride suspension. The mixture was stirred at ambient temperature for three hours. Water (10 ml) was added dropwise, followed by 2N hydrogen chloride (30 ml). The mixture was extracted with diethyl ether (3×150 ml) to yield a light purple oil.

6-Methyl indole 6-hydroxymethyl indole (6.135 g, 41.69 mmol) was dissolved in ethanol (70 ml). 10% Palladium on charcoal (0.610 g) was suspended in acetic acid (70 ml) and added to the ethanol (70 ml) solution. The mixture was placed on the high pressure hydrogenator at 60 psi. After 20 hours, the mixture was filtered through Celite and the resulting solution concentrated in vacuo. The mixture was purified by flash chromatography using chloroform as solvent to yield a colourless oil.

6-Methyl indole-3-carboxaldehyde

Phosphorus oxychloride (3.2 ml, 34.3 mmol) was added dropwise to dimethyl formamide (26 ml) over ten minutes at ~5° C. To this solution was added a dimethyl formamide (32 ml) solution of 6-methylindole (3.307 g, 25.2 mmol) over 10 minutes. The mixture was slowly warmed to ambient temperature, then heated to 50° C. for four hours. The mixture was cooled to ambient temperature, then poured onto ice (500 g). The aqueous solution was left to stand for 16 hours. Sodium hydroxide (6.0 g) was dissolved in water (22 ml) and added dropwise to the brown solution. The resultant yellow precipitate was boiled and filtered hot. It was left to cool to room temperature, then to 5° C. The precipitate was filtered off and washed with water (800 ml), dried at the pump, then further dried in vacuo at 50° C. for 16 hours to yield a yellow solid.

6-Methyl-3-(2-nitroethylidenyl)-1H-indole

6-Methylindole-2-carboxaldehyde (3.5 g, 21.99 mmol) was suspended in nitromethane (60 ml). Ammonium acetate (0.562 g, 7.3 mmol) was added and the mixture was refluxed under nitrogen for three hours. The mixture was cooled and a further amount of ammonium acetate (0.762 g, 9.9 mmol) was added. The mixture was refluxed for a further nine hours, then left to stand for 13 hours at ambient temperature. It was further cooled in an ice bath, filtered in vacuo and sucked dry, and then further dried in vacuo at 50° C. to yield an orange solid.

6-Methyltryptamine

Lithium aluminium hydride (3.993 g, 105 mmol) was suspended in sodium-dried tetrahydrofuran (95 ml). The suspension was cooled using an ice bath. 6-Methyl-3-(2-nitro-ethylidene)indole (3.723 g, 18.41 mmol) was added dropwise as a tetrahydrofuran (80 ml) over 15 minutes. The mixture was refluxed under nitrogen for 16 hours, cooled to ambient temperature, then further cooled with an ice bath. Water (120 ml) was added dropwise to the mixture. Diethyl ether (200 ml) was added and the organic solution was decanted off. The aqueous phase was extracted with diethyl ether (2×200 ml). The ether fractions were combined and washed with 2N hydrochloric acid (2×200 ml). The aqueous layer was separated and basified with 50% sodium hydroxide solution to pH12. It was extracted with diethyl ether (2×200 ml), separated and dried over magnesium sulphate, and filtered and concentrated in vacuo to yield a cream solid.

1-[2-(7-Methyl-1,2,3,4-tetrahydro-9H-pyrido[3,4-b]indole-2-yl-1-ethyl]-1,3-dihydro-2H-benzimidazol-2-one 7-Methyl-1,2,3,4-tetrahydro-9H-pyrido[3,4-b]indole (0.400 g, 21.4 mmol) was dissolved in N-methyl pyrolidone (5 ml). To this mixture was added 1-chloroethyl-1,3-dihydro-2H-benzimidazol-2-one (0.454 g, 2.31 mmol), potassium carbonate (0.739 g, 5.35 mmol) and sodium iodide (0.385 g, 2.57 mmol). These components were heated to 80° C. under nitrogen for three hours. The mixture was cooled to room temperature and poured onto ice (20 g). The resulting precipitate was filtered and washed with water (3×20 ml). It was dried in vacuo at 50 C. and purified using flash silica/chloroform/methanol, to yield a yellow solid, melting point 119°–121° C.

The following compounds were prepared in a similar way:

1-[2-(8-Chloro-1,2,3,4-tetrahydro-9H-pyrido[3,4-b]indol-2-yl)-1-ethyl]-1,3-dihydro-2H-benzimidazol-2-one, melting point 110°–112° C.

1-[2-(7-Methoxy-1,2,3,4-tetrahydro-9H-pyrido[3,4-b]indol -2-yl)-1-ethyl]-1,3-dihydro-2H-benzimidazol-2-one, melting point 105°–107° C.

EXAMPLE 10

7-Fluoro-2,3,4,5-tetrahydro-1H-pyrido[4,3-b]-indole

4-Piperidone hydrochloride monohydrate (4.55 g) and 3-fluorophenylhydrazine hydrochloride (4.85 g) were added to ethanol (80 ml) and the mixture was heated under reflux for one hour. Hydrogen chloride gas was bubbled into the mixture and refluxing was recommenced for another 1.5 hours. The solution was cooled to 0° C., the hydrochloride was filtered off, washed with ethanol, dissolved in boiling water, decolourised with activated charcoal and filtered. 2M Sodium hydroxide solution was added to the warm solution until it was neutral when tested with pH paper. The pale cream solid was filtered off, washed with water and dried. Recrystallisation from acetonitrile gave a white solid which was a mixture of 7-fluoro and 9-fluoro-isomers in a ratio of 86:14 respectively (HPLC).

This method was used (J. Chem. Soc. (C), 1968, 1235–1243) to make the known compounds:

8-Fluoro-2,3,4,5-tetrahydro-1H-pyrido[4,3-b]indole, melting point 210° C. (U.S. Pat. No. 3,419,568) (from 4-fluorophenylhydrazine hydrochloride.)

2,3,4,5-Tetrahydro-1H-pyrido[4,3-b]indole, melting point 226° C. (J. Chem. Soc. (C), 1968, 1235–1243, and J. Med. Chem. 1966, 436–438) (from phenylhydrazine hydrochloride.)

and

6-Fluoro-2,3,4,5-tetrahydro-1H-pyrido[4,3-b]indole, melting point 220° C. (from 2-fluorophenylhydrazine hydrochloride).

1-[2-(2,3,4,5-(Tetrahydro-1H-pyrido[4,3-b]indol-2-yl)-1-ethyl]-1,3-dihydro-2H-benzimidazol-2-one 2,3,4,5-Tetrahydro-1H-pyrido[4,3-b]indole (2.15 g) was dissolved in dry acetonitrile (150 ml). To this was added a catalytic amount of sodium iodide, potassium carbonate (2.25 g) and 1-chloroethyl-1,3-dihydro-2H-benzimidazol-2-one (2.8 g). The mixture was heated, with stirring, under reflux for 48 hours, and the hot solution was filtered off from inorganic material and evaporated in vacuo. The residue was triturated with ethanolic hydrogen chloride. The hydrochloride was filtered and washed with ethanol, dissolved in boiling water, filtered and basified with 50% sodium hydroxide solution. The solid was filtered, washed with water and dried. The crude solid was dissolved in 5% methanol in chloroform drawn through a pad of 'flash' silica, evaporated, and triturated with acetonitrile. The solid was filtered and washed with ethanol. The solid was recrystallised from dioxan to give the monodioxanolate, melting point 114°–117° C.

The following compounds were prepared in a similar way:

1-[2-(8-Fluoro-2,3,4,5-tetrahydro-1H-pyrido[4,3-b]indol-2-yl)-1-ethyl]-1,3-dihydro-2H-benzimidazol-2-one, melting point 200.5°–201.5° C. (from 8-fluoro-2,3,4, 5-tetrahydro-1H-pyrido[4,3-b]indole).

1-[2-(6-Fluoro-2,3,4,5-tetrahydro-1H-pyrido[4,3-b]indol-2-yl)-1-ethyl]-1,3-dihydro-2H-benzimidazol-2-one hydrochloride, melting point 214°–216° C. (from 6-fluoro-2,3,4,5-tetrahydro-1H-pyrido[4,3-b]indole).

and

1-[2-(7-Fluoro-2,3,4,5-tetrahydro-1H-pyrido[4,3-b]indol-2-yl)-1-ethyl]-1,3-dihydro-2H-benzimidazol-2-one, melting point 125°–127° C. This contained between 6 and 10% of the 9-isomer (from 7-fluoro-2,3,4,5-tetrahydro-1H-pyrido[4,3-b]indole (+14% 9-isomer)).

EXAMPLE 11

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 12

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatine capsules in 200 mg quantities.

We claim:

1. A compound of the formula:

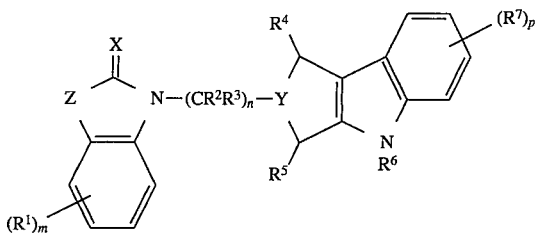

in which $R^1$ and $R^7$ are each halo, trifluoromethyl, $C_{1-6}$ alkyl, $C_{1-6}$ alkoxy, optionally substituted phenyl, optionally substituted naphthyl or optionally substituted heteroaryl, $R^2$ and $R^3$ are each hydrogen or $C_{1-6}$ alkyl, $R^4$ and $R^5$ are each hydrogen, halo, trifluoromethyl, $C_{1-6}$ alkyl, $C_{1-6}$ alkoxy, optionally substituted phenyl, optionally substituted naphthyl or optionally substituted heteroaryl, $R^6$ is hydrogen, $C_{1-6}$ alkyl, optionally substituted phenyl, optionally substituted naphthyl, optionally substituted heteroaryl, optionally substituted phenyl-$C_{1-6}$ alkyl or —$CO_2R^8$ where $R^8$ is an ester group, m and p are each 0, 1, 2, 3 or 4, n is 1, 2, 3 or 4, Z is

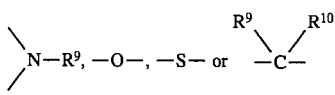

where $R^9$ and $R^{10}$ are each hydrogen, $C_{1-6}$ alkyl or optionally substituted phenyl-$C_{1-6}$ alkyl, X is oxygen or sulphur, and Y is

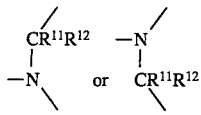

where $R^{11}$ and $R^{12}$ are each hydrogen, $C_{1-6}$ alkyl, trifluoromethyl, optionally substituted phenyl, optionally substituted naphthyl or optionally substituted heteroaryl; and salts and solvates thereof.

2. A compound according to claim 1 of the formula:

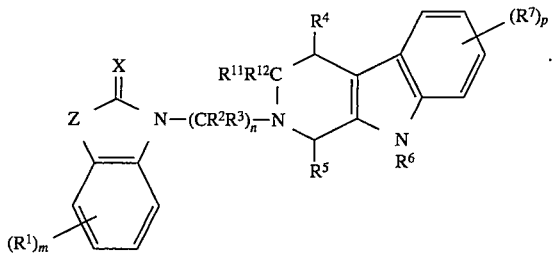

3. A compound according to claim 2 in which X is oxygen.

4. A compound according to claim 3 in which Z is

and $R^9$ is hydrogen or $C_{1-6}$ alkyl.

5. A compound according to claim 1 in which Z is

X is oxygen, where $R^9$ is hydrogen or $C_{1-6}$ alkyl, m is 0,1 or 2, n is 1 or 2 and $R^4$, $R^5$ and $R^6$ are hydrogen.

6. A compound of the formula:

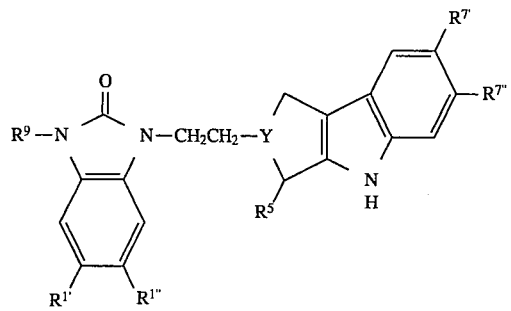

in which $R^9$ is hydrogen or $C_{1-6}$ alkyl, $R^{1'}$, $R^{1'''}$, $R^{7'}$ and $R^{7''}$ are each hydrogen, halo, $C_{1-6}$ alkyl or $C_{1-6}$ alkoxy, $R^5$ is hydrogen or trifluoromethyl, and Y is:

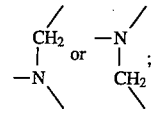

and salts thereof.

7. A pharmaceutical formulation comprising a compound according to claim 1 or a pharmaceutically-acceptable salt or solvate thereof, together with a pharmaceutically acceptable diluent or carrier therefor.

8. A method for treating a disorder of the central nervous system which comprises administering an effective amount of a compound according to claim 1, or a pharmaceutically-acceptable salt or solvate thereof.

* * * * *

UNITED STATES PATENT AND TRADEMARK OFFICE
CERTIFICATE OF CORRECTION

PATENT NO. : 5,563,147

DATED : October 8, 1996

INVENTOR(S) : Jeremy Gilmore, et al.

It is certified that error appears in the above-indentified patent and that said Letters Patent is hereby corrected as shown below:

On the title page, item [54] and column 1, line 1, delete SEROTONERBIC" and insert --SEROTONERGIC--.

Signed and Sealed this

Eighteenth Day of February, 1997

Attest:

BRUCE LEHMAN

*Attesting Officer*     *Commissioner of Patents and Trademarks*